United States Patent [19]

Stevenson et al.

[11] Patent Number: 5,532,401
[45] Date of Patent: Jul. 2, 1996

[54] PROCESS FOR PRODUCTION OF TRIS(NONYLPHENYL) PHOSPHITE

[75] Inventors: Donald R. Stevenson; Daniel L. Clark; John C. Debevec, all of Dover, Ohio; Charles N. Slater, Houston, Tex.; Carroll W. Larke, Zoar, Ohio

[73] Assignee: Dover Chemical Corporation, Dover, Ohio

[21] Appl. No.: 375,557

[22] Filed: Jan. 19, 1995

[51] Int. Cl.⁶ ............................................. C07F 9/08
[52] U.S. Cl. ............................................. 558/95; 558/90
[58] Field of Search ..................................... 558/95, 90

[56] References Cited

U.S. PATENT DOCUMENTS

| | | | |
|---|---|---|---|
| 3,351,683 | 11/1967 | Wu et al. | 260/982 |
| 3,823,207 | 7/1974 | Herzog et al. | 260/976 |
| 4,086,304 | 4/1978 | Hutton et al. | 260/989 |
| 5,298,541 | 3/1994 | Böhshar et al. | 524/126 |
| 5,322,871 | 6/1994 | Pitteloud et al. | 524/151 |
| 5,401,845 | 3/1995 | Pitteloud et al. | 546/25 |

*Primary Examiner*—Joseph K. McKane
*Attorney, Agent, or Firm*—Oldham & Oldham, Co.

[57] ABSTRACT

An improved process for the preparation of tris(nonylphenyl) phosphite is described which includes the steps of combining at least a 4 weight percent excess of nonylphenol (preferably 8 weight percent excess) with $PCl_3$ with agitation and heating sufficient to liberate HCl formed during the synthetic reaction as a by-product and removing the excess nonylphenol from the tris(nonylphenyl) phosphite by thin film distillation to reduce the residual chloride level to 90 ppm or less, an acid number of 0.1 or less and a nonylphenol content after stripping of 0.1 weight percent or less. The temperature of the reaction was from room temperature to 130° C., and the temperature of the evaporator which removes the excess nonylphenol is from 100° C. to 350° C., preferably from 150° C. to 250° C., under a system vacuum of from 0.01 mm Hg to 5 mm Hg.

14 Claims, No Drawings

PROCESS FOR PRODUCTION OF TRIS(NONYLPHENYL) PHOSPHITE

TECHNICAL FIELD

The invention described herein pertains generally to a process for producing pure tris(nonylphenyl) phosphite, the phosphite having a low level of free nonylphenol, a low level of chloride and a very low acid number. This is done by reacting phosphorus trichloride ($PCl_3$) with an excess (6% or greater) of p-nonylphenol, thereby forcing the reaction to completion. When the reaction is complete, excess nonylphenol is distilled from the tris(nonylphenyl) phosphite using thin film distillation.

BACKGROUND OF THE INVENTION

Tris(nonylphenyl) phosphite (TNPP) has been used for years to stabilize polymers, especially synthetic rubber products against oxidation and color degradation. The use of phosphites as stabilizer for synthetic rubbers requires that they be usually incorporated into an aqueous synthetic rubber latex prior to flocculation and drying. This means that the phosphite should have good hydrolytic stability for treating these emulsions. Tris(nonylphenyl) phosphite (TNPP) has been a standard phosphite that has been used for this application. Phosphites of this type function as stabilizers for polymers and especially synthetic rubbers by reacting with hydroperoxides forming a phosphate and a corresponding alcohol. The reduction of the peroxides slows crosslinking and color degradation. Unfortunately, organic triphosphites also hydrolyze quite readily by reacting with moisture to form a dialkyl or diaryl hydrogen phosphite. The di-substituted phosphites are not as active as tri-phosphites in decomposing hydroperoxides. Therefore, it is desirable to have a hydrolytically stable organic triphosphite so it can function over a longer period of time.

Tris(nonylphenyl) phosphite (TNPP) has been made more hydrolytically stable by the addition of amines such as tris(isopropanol) amine (TiPA). Both tris(nonylphenyl) phosphite and tris(isopropanol) amine are FDA sanctioned for use in many polymer applications. However, this is a non-satisfactory solution since the amine additive is effective only for a short period of time, and cannot be used for some purposes, such as for example, in a stabilizer composition for polyvinyl chloride (PVC) which may come in contact with food.

It has also been found that the presence of excess nonylphenol from the synthesis of tris(nonylphenyl) phosphite used to stabilize a polymer, may contribute to some color degradation. The excess nonylphenol is also volatile and has a tendency to form a sticky substance on drying equipment and processing equipment. Another very recent cause for concern regarding the presence of excess nonylphenol is the fact that it has been implicated as an estrogen mimic. Based on all of these facts, it would be very desirable to produce a pure tris(nonylphenyl) phosphite which has a low acid number, low residual chloride content and a very low level of free nonylphenol.

Tris(nonylphenyl) phosphite (TNPP) is typically produced by reacting phosphorus trichloride with an excess of nonylphenol, typically from 2–6% by weight excess nonylphenol. The reaction is left to proceed until a low acid number is obtained. Faster reaction times and lower acid numbers are obtained if a large excess of nonylphenol is used, such as >5% excess nonylphenol. If a lower percentage of nonylphenol is used, e.g., <4%, the reaction time to produce a low acid number is very long and typically a high chloride product is obtained. A high chloride product is undesirable due to the corrosive nature of chloride on processing equipment for polymers. Also, a high chloride content, typically results in poor hydrolytic stability. So the compromise is to have sufficient nonylphenol to force the reaction to completion thereby achieving low chloride and low acid numbers, but also within a reasonable reaction time.

SUMMARY OF THE INVENTION

In accordance with the present invention, there is provided a process by which tris(nonylphenyl) phosphite (TNPP) is formed using an excess amount of nonylphenol, thereby forcing completion of the synthetic reaction, but whereinby through evaporative techniques, a low chloride number coupled with a low acid number is achieved in the final product.

It is an object of this invention to provide a reaction wherein the superior tris(nonylphenyl) phosphite (TNPP) product (very low acid number, a very low chloride content and a very low level of free nonylphenol) is achieved through the reaction of phosphorus trichloride ($PCl_3$) with a large excess of nonylphenol, typically 6% or greater excess by weight nonylphenol, thereby resulting in a fast reaction time where the excess nonylphenol reacts with all the $PCl_3$ to liberate HCl.

It is a further object of this invention to provide a process of synthesizing a superior tris(nonylphenyl) phosphite (TNPP) product wherein the excess nonylphenol is then distilled from the phosphite using thin film distillation.

These and other objects of this invention will be evident when viewed in light of the detailed description, and appended claims.

DETAILED DESCRIPTION OF THE INVENTION

The best mode for carrying out the invention will now be described for the purposes of illustrating the best mode known to the applicant at the time. The examples are illustrative only and not meant to limit the invention, as measured by the scope and spirit of the claims.

One of the elements of the invention lies in the recognition of the desirability of using excess nonylphenol, at least 2 weight percent, more preferably at least 6 weight percent, and in a most preferred embodiment, at least 8 weight percent. In a commercial environment, the amount of excess nonylphenol is typically no more than about 15 weight percent. The use of excess nonylphenol not only decreases the necessary reaction time, but quite unexpectedly, it reduces the amount of residual chloride present in the tris(nonylphenyl) phosphite product. It additionally decreases the final acid number of the phosphite product.

These beneficial results were achieved by using an excess of nonylphenol in the preparation of the product, thereby increasing the reaction rate during the synthesis, with subsequent removal by the use of vacuum thin film distillation technique, e.g., at vacuum levels of from 1–10 mm Hg, typically 0.01–5 mm Hg, and temperatures of 100° C. and above (e.g., 350° C.), more preferably between 150° C.–250° C. When using higher vacuums, the use of a nitrogen sparge may be considered useful to perform the separation at lower vacuum levels. In particular, a wiped film evaporator was found to be effective when operating at an evaporator temperature of 198°–202° C., a system vacuum of 0.1–0.15 mm Hg, and a feed rate of 80–100 g/hr. Based upon the equipment used, which had an evaporative surface area of 50 in² and a rotor speed of 465 rpm, the product residence time was in the 4–5 second range.

In one embodiment of the invention, the feed was preheated to approximately 80° C., thereby maintaining a temperature differential of less than 150° C. between the feed temperature and evaporator surface temperature.

EXAMPLES

The following reaction of combining nonylphenol with phosphorus trichloride ($PCl_3$) was followed in preparing the tris(nonylphenyl) phosphite (TNPP).

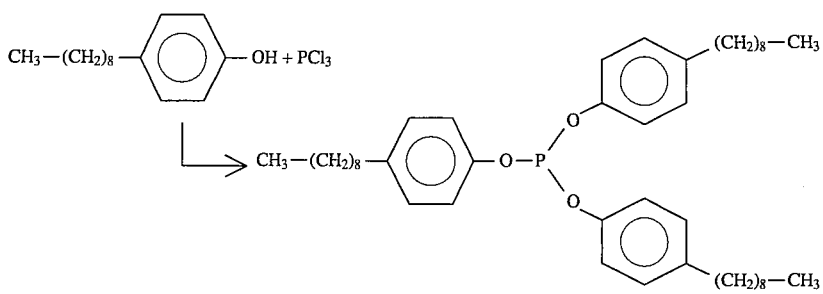

Example #1

To a 3 liter flask equipped with a heating mantle, temperature control, gas inlet, and gas outlet, and addition funnel, 970 grams of nonylphenol (4 moles), 10% by weight excess, was added. At 30° C., 183 grams (1.33 moles) of $PCl_3$ was slowly added to the nonylphenol with agitation resulting in the liberation of HCl which was collected in a flask containing water. $PCl_3$ addition continued over a period of about 1 hour. At the end of the $PCl_3$ addition, the temperature was increased to 50° C. and held for another hour. At the end of this additional hour, the temperature was increased gradually to 130° C. After further reaction for 8–10 hours, it was determined that the rate of HCl liberation is nil, due to the use of excess nonylphenol forcing the reaction to completion. The acid number was measured to be <0.05. The product was then run through a thin film distillation (e.g., Pope still) at a temperature of 200° C. and a vacuum of 1 mm. The resulting bottoms product, tris(nonylphenyl) phosphite (TNPP), had an analysis of approximately 0.1% free nonylphenol, an acid number of 0.01 and a very low chloride content, (<20 ppm). Tris(nonylphenyl) phosphite (TNPP) produced by this process was very pure. When this product was tested for hydrolytic stability, it was surprising to find that it had excellent hydrolytic stability compared to tris(nonylphenyl) phosphite (TNPP) prepared by a standard process using stoichiometric amounts of reactants (Example #4).

Example #2 (TNPP-2)

The same procedure was employed as that described for Example #1, using the quantities of reactants described in col 3, of Table I (i.e., 8.0 weight percent excess of nonylphenol) with characterization data as provided in col 3 of the Table.

Example #3 (TNPP-3)

The same procedure was employed as that described for Example #1, using the quantities of reactants described in col 4, of Table I (i.e., 4.0 weight percent excess of nonylphenol) with characterization data as provided in col 4 of the Table. No distillation was performed on this product.

Example #4 (TNPP-1)

The same procedure was employed as that described for Example #1, using the quantities of reactants described in col 2, of Table I (i.e., stoichiometric quantities of reagents) and used as a bench mark sample. No distillation was performed on this product.

Hydrolytic Stability Testing Protocol

The hydrolytic stability test used involved mixing tris(nonylphenyl) phosphite (TNPP) using oleic acid, sodium hydroxide emulsion and then checking the pH after 90 minutes at 80° C. oven aging. Specifically, the test involved:

(1) Weighing 2.9 g of oleic acid into a 150 ml beaker, warming slightly with mixing on a heated magnetic stirrer;

(2) Weighing 4.21 grams of 10% NaOH (wt to vol), 2.5N into a 50 ml beaker;

(3) Warming 9.25 ml deionized water in 50 ml beaker to 50° C.;

(4) Adding the diluted NaOH to the oleic acid and mixing until homogeneous on the stirring hotplate, keeping the mixture warm;

(5) Weighing 25.0 g of TNPP into a 250 ml beaker and warming slightly to assure good mixing with stirring on the hot plate;

(6) Adding the sodium oleate mixture to the phosphite, followed by rinsing with 19.45 ml, 50° C. deionized water to assure all the sodium oleate has been added;

(7) Vigorously stirring with the magnetic stir plate for 15 minutes;

(8) Pouting the sample of the dispersion into a 50 ml beaker;

(9) Heating the remaining mixture in an oven at 80° C.±2° C. for 90 minutes, and covering tightly with saran wrap;

(10) Measuring the pH at 25° C. after calibrating with pH 7 and pH 10 certified buffers;

(11) Removing the remaining mixture from the oven after 90 min., cooling with mixing on the stir plate until 25° C. and recording the pH; and

(12) Repeating the pH measurement of sample #11, mixing at room temperature after the passage of an additional 24 and 48 hours.

The results showed that tris(nonylphenyl) phosphite (TNPP) prepared using an excess of nonylphenol gave better hydrolytic stability than standard tris(nonylphenyl) phosphite (TNPP) prepared using stoichiometric amounts of reactants.

TABLE I

|  | TNPP-1 | TNPP-2 | TNPP-3 |
|---|---|---|---|
| $PCl_3$ (moles) | 1.0 | 1.0 | 1.0 |
| Nonylphenol (moles) | 3.0 | 3.25 | 3.13 |
| Excess Nonylphenol (wt. %) | 0 | 8.0 | 4.0 |
| Rxn. Time (hrs) | 48 | 16 | 24 |
| Nonylphenol content (wt. %) | 3.0 | 9.5 | 5.0 |
| NP content after strip (wt. %) | N.A. | 0.1 | N.A. |
| Final acid nbr. mg KOH/gram | 0.2 | 0.01 | 0.1 |
| Chlorides (ppm) | 360 | <20 | 90 |
| Hydrolytic Stability |  |  |  |
| Initial pH | 11.8 | 12.1 | 12.0 |
| 90 min. pH | 11.3 | 12.0 | 11.9 |
| 1 day pH | 10.6 | 11.9 | 11.6 |
| 2 day pH | 10.3 | 11.8 | 11.2 |

The results shows that making tris(nonylphenyl) phosphite (TNPP) by adding excess nonylphenol at the start, and then snipping off the excess with thin film distillation (as shown in TNPP-2), gives a superior product in regard to (1) low chlorides, (2) low nonylphenyl; and (3) good hydrolytic stability, which is probably due to the low acid number and the low chlorides present. The pure TNPP produced by the described method above, having a low free nonylphenol (<1.0%) is also an improved stabilizer for polyolefins, particularly when compared to TNPP prepared by standard preparative techniques, where the level of free nonylphenol is greater than 1.5%. This TNPP can also be reacted with tris(isopropanol) amine (TiPA) before or after thin film distillation to give a TNPP product with very good hydrolytic stability.

While the use of TNPP is envisioned to be particularly useful i the stabilization of polyolefins, the additive is useful in other polymeric systems, e.g., polyvinyl chloride and polyesters.

The invention has been described with reference to preferred and alternate embodiments. Obviously, modifications and alterations will occur to others upon the reading and understanding of the specification. It is intended to include all such modifications and alterations insofar as they come within the scope of the appended claims or the equivalents thereof.

What is claimed is:

1. An improved process for the preparation of tris-(nonylphenyl) phosphite comprising the steps of:
    (a) combining at least a 2 weight percent excess of nonylphenol with $PCl_3$ with agitation and heating sufficient to liberate HCl formed during the synthetic reaction as a by-product; and
    (b) removing the excess nonylphenol from the tris-(nonylphenyl) phosphite by thin film distillation to reduce the residual chloride level to 20 ppm or less, an acid number of 0.1 or less and a nonylphenol content after stripping of 0.5 weight percent or less.

2. The process of claim 1 wherein the temperature of the reaction was from room temperature to 250° C.

3. The process of claim 2 wherein the temperature of the thin film distillation was from 100° C. to 350° C.

4. The process of claim 3 wherein the vacuum is from 0.01 mm Hg to 10 mm Hg.

5. The process of claim 4 wherein the temperature of the thin film distillation was from 150° C. to 250° C.

6. The process of claim 5 wherein the feed into the thin film distillation is preheated.

7. The product of the process of claim 5.

8. The process of claim 1 wherein the weight percent excess of nonylphenol is at least 4 percent.

9. The process of claim 8 wherein the temperature of the reaction was from room temperature to 250° C.

10. The process of claim 9 wherein the temperature of the thin film distillation was from 100° C. to 350° C.

11. The process of claim 10 wherein the vacuum is from 0.01 mm Hg to 10 mm Hg.

12. The process of claim 11 wherein the temperature of the thin film distillation was from 150° C. to 250° C.

13. The process of claim 12 wherein the feed into the thin film distillation is preheated.

14. An improved process for the preparation of tris-(nonylphenyl) phosphite which includes the steps of combining at least a 2 weight percent excess of nonylphenol with $PCl_3$ with agitation and heating sufficient to liberate HCl formed during the synthetic reaction as a by-product wherein the improvement comprises the use of a thin film distillation post processing step under vacuum of between 0.01–10 mm Hg at a temperature of from 100° C. to 350° C. to remove excess nonylphenol from the tris(nonylphenyl) phosphite reducing the residual chloride level to 20 ppm or less, an acid number of 0.1 or less and a nonylphenol content after stripping of 0.5 weight percent or less.

\* \* \* \* \*